United States Patent
Saint-Jalmes

(10) Patent No.: US 7,534,906 B2
(45) Date of Patent: May 19, 2009

(54) PROCESS FOR THE SYNTHESIS OF HYDROGENOFLUOROMETHYLENE- SULPHONYL RADICAL DERIVATIVES

(75) Inventor: Laurent Saint-Jalmes, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 279 days.

(21) Appl. No.: 10/519,287

(22) PCT Filed: Jun. 24, 2003

(86) PCT No.: PCT/FR03/01940

§ 371 (c)(1),
(2), (4) Date: Nov. 25, 2005

(87) PCT Pub. No.: WO2004/002951

PCT Pub. Date: Jan. 8, 2004

(65) Prior Publication Data

US 2006/0178536 A1    Aug. 10, 2006

(30) Foreign Application Priority Data

Jun. 28, 2002    (FR) ................... 02/08090

(51) Int. Cl.
*C07C 309/00*    (2006.01)
*C07C 303/00*    (2006.01)
(52) U.S. Cl. ........................................ 558/44; 562/114
(58) Field of Classification Search ................. 562/114; 558/44
See application file for complete search history.

(56) References Cited

U.S. PATENT DOCUMENTS 6,316,636 B1 *  11/2001  Janin et al. ............... 548/375.1

OTHER PUBLICATIONS

Moore, George G.I., *Fluoroalkanesulfonyl Chlorides*, J. Orgt. Chem, vol. 44, No. 10, 1979, St. Paul, MN.
Langlois, Bernard R., *Improvement of the Synthesis of Aryl Difluoromethyl Ethers and Thioethers by Using A Solid-Liquid Phase-Transfer Technique*, Journal of Fluorine Chemistry, 41, pp. 247-261, 1988, The Netherlands.
Feldhoff et al., *Darstellung und Eigenschaften Trifluormethyl- und Trifluormethylchalkogenyl-substituierter Adamantane*, Journal of Fluorine Chemistry, 67, pp. 245-251, 1994, The Netherlands.
International Search Report, WO 2004/002951 A3, Dec. 16, 2003.

* cited by examiner

*Primary Examiner*—Kamal A Saeed
*Assistant Examiner*—Samantha L Shterengarts
(74) *Attorney, Agent, or Firm*—Buchanan, Ingersoll & Rooney P.C.

(57) ABSTRACT

The invention concerns a method for synthesis of hydrogenofluoromethylenesulphonyl radical derivatives, comprising: a) a step which consists in condensing a thiolate (that is a monoalkyl sulphide salt) with a compound having a sp; 3hybridized carbon bearing a hydrogen, a fluorine, a heavy halogen selected among chlorine, bromine and iodine and an electron-attracting group selected among fluorine and those whereof the; is not less than 0.2, advantageously than 0.4; b) a step which consists in oxidizing the compound obtained in step a). The invention is applicable to the synthesis of various compounds having a suphinyl or sulphonyl group.

12 Claims, No Drawings

PROCESS FOR THE SYNTHESIS OF HYDROGENOFLUOROMETHYLENESULPHONYL RADICAL DERIVATIVES

This application is an application under 35 U.S.C. Section 371 of International Application Number PCT/FR2003/001940 filed on Jun. 26, 2003.

The subject matter of the present invention is a novel synthesis of derivatives comprising a hydrofluoromethylenesulfonyl or -sulfinyl radical.

It is targeted more particularly at the synthesis of difluoromethanesulfinic or -sulfonic acid derivatives and in particular the acid proper, its salts and its acid chlorides.

The sulfonic acids carried by electron-withdrawing groups and in particular carried by electron-withdrawing groups where the carbon carrying the sulfonic functional group also carries at least one fluorine are increasingly advantageous compounds, first because they make it possible to give specific particular properties to medicaments or to agricultural derivatives and, secondly, because they can act as constituent components of salts for batteries, in particular "lithium" batteries.

Sulfonyl and sulfinyl halides should be indicated in particular among advantageous products. Mention may be made, among the halides, of the bromide, which is relatively unstable, the chloride and the fluoride.

The processes for producing these compounds are generally lengthy and difficult or give relatively low yields, or else require the use of particularly extensive solvents or operating conditions.

If reference is made more specifically to difluoromethanesulfonic acid, sometimes known as diflic acid, its synthesis is not described to any great extent in the literature and requires the use of relatively expensive solvents and requires the formation of a large amount of salts.

This is why one of the aims of the present invention is to provide a process for the synthesis of acids or acid derivatives comprising a hydrofluoromethylenesulfonyl or -sulfinyl radical which makes it possible to avoid the use of solvents which are expensive, unstable or difficult to employ.

Another aim of the present invention is to provide a reaction of the above type which makes it possible to obtain good yields and in particular high conversion yields (CY, that is to say the yield of desired product obtained with respect to the amount of starting material consumed), that is to say of greater than 60%, preferably greater than 70%.

Another aim of the present invention is to provide a process which is multipurpose in nature, so that it can result equally well in the formation of acid salts, of acids or of acid halides.

It is also desirable for it to be possible to obtain essentially the acid corresponding to the sulfonic radical.

Another aim of the present invention is to provide a process which makes it possible to obtain derivatives of sulfinic nature.

These aims, and others which will become apparent subsequently, are achieved by means of a process for the synthesis of derivatives comprising a hydrofluoromethanesulfonyl or -sulfinyl radical comprising at least the following stages:

a) a stage of condensation in a solvent of a thiolate (that is to say, a monoalkyl sulfide salt), the counterion (that is to say, the cation providing the electrical neutrality of the molecule) of which is advantageously nonbasic (that is to say, a cation which is hydrolyzed, for concentrations of $10^{-2}$N, only at pH values of greater than 10, advantageously than 12), with a compound exhibiting a carbon of $sp^3$ hybridization carrying a hydrogen, a fluorine, a heavy halogen, chosen from chlorine, bromine and iodine, and an electron-withdrawing group chosen from fluorine and those for which the $\sigma_p$ is at least equal to 0.2, advantageously to 0.4;

b) a stage of oxidation, advantageously of halogenation, preferably of chlorination or of bromination, in the presence of an aqueous phase;

said solvent of stage a) being chosen from water-immiscible solvents, from aqueous phases and from the two-phase combination of a water-immiscible solvent and of an aqueous phase, said aqueous phases comprising at most ⅓ by weight of water-miscible nonaqueous solvent; the ratio of the amount in equivalents of the thiolate to the amount in moles of water being at most equal to 50.

When use is made of an aqueous phase comprising a water-miscible nonaqueous solvent, it is preferable for this solvent not to be base-sensitive, that is to say for it not to be destroyed by the presence of base; in particular, soluble esters and amides are to be avoided as far as possible. The expression "water-miscible" should be understood as meaning a solvent miscible in all proportions with water. The water-immiscible solvents are advantageously chosen from those which exhibit a solubility in water, by weight, of at most 10%, that is to say for the water to be able to dissolve at most 10%, under standard temperature and pressure conditions, of the water-immiscible solvent. Use may be made, as water-immiscible solvent, of chlorinated aromatic derivatives, indeed even certain ethers.

It is also preferable for the solubility in water of said immiscible solvent to be at most 5% by weight, preferably 2% by weight.

Particular mention may be made, among immiscible solvents, of aromatic derivatives, optionally substituted, and in particular haloaromatic derivatives, such as mono-, di- or trichlorobenzenes.

Anisole, like the other phenol ethers, may be advantageous. However, the activation by the oxygen or by aromatic ring hydrogen of aliphatic nature can interfere in the second stage and, in that case, it would be advisable to remove the solvent before the "halogenation" stage.

However, according to the present invention, it is preferable to use, as solvent, an aqueous phase comprising little or, preferably, no miscible organic solvent but which can comprise dissolved salts and in particular hydrosoluble bases.

An important point of the present invention is that, in order to maximize the yield, it is highly preferable to use a small amount of water. Thus, it is preferable for the ratio of the amount, expressed in equivalents, of the thiolate to the amount, expressed in moles, of water to be at most equal to 30, advantageously to 20.

The amount of thiolate is expressed in equivalents in order to take into account the case where use would be made of compounds comprising two sulfide functional groups or two thiolate functional groups. It is even possible to envisage, although doubtless not very advantageous economically, to use compounds comprising multiple thiol functional groups. According to the present invention, it is preferable for the amount of water to be sufficiently high to form a significant phase. Thus, the ratio of the amount, in equivalents, of the alkyl sulfide to the amount of water (in the basic phase or phases), expressed in moles, is at least equal to 0.5, advantageously to 1, preferably to 1.5.

According to the present invention, it is preferable for said aqueous phases to comprise at most a quarter by weight of nonaqueous solvent, preferably at most a tenth.

It is also preferable for the $[H_2O]/([H_2O]+[\text{water-miscible solvent}])$ molar ratio to be at least equal to 0.9, advantageously to 0.95. Finally, it is preferable to limit the concentration of the base in the aqueous phase to 0.5 equivalent per kg of aqueous phase.

It should be pointed out that the cationic thiolate which constitutes one of the substrates of stage A can be prepared in situ by the action of a sulfide R—SH on a stronger base than R—S⁻.

The limitation on the concentration of the base and in particular of OH⁻ is targeted only at the excess of base and thus does not take into account the amount of base consumed in preparing the thiolate.

The thiolate can be written under the general formula R—S-M, where M corresponds to a metal or to a cation which, in combination with the OH⁻ anion, constitutes a strong base, that is to say a base having an associated acid exhibiting a pKa at least equal to 10, advantageously to 12, preferably to 14.

The present invention can, in some cases, in particular when there is an organic phase comprising a water-immiscible organic solvent, a phase transfer agent. These agents are well known to a person skilled in the art and can in particular be chosen from oniums and from iniums, from crown ethers or from cryptand ethers, such as TDA1 (N[CH₂—CH₂—O—CH₂—CH₂]₃N). According to the present invention, it is preferable to operate with a small amount (or excess with respect to the amount necessary to neutralize the thiol to thiolate) of base in the aqueous phase, this amount advantageously being at least equal to 5%, advantageously to 10%, of the amount of said thiolate (R—S-M).

However, it is preferable for the aqueous medium of stage a) to comprise an amount of base at most equal to one times the amount of said thiolate, preferably at most 50%, more preferably at most 30%.

According to the present invention, it has been shown that it is desirable to use sulfides carried by an alkyl which is tertiary or of benzylic or allylic nature.

This activation of the carbon carrying the sulfur makes it possible to facilitate the carbon-sulfur cleavage which is carried out in stage b). However, as the allylic radical is liable to result in troublesome side reactions and polymerizations, it is preferable for the alkyl derivatives to be restricted to those of tertiary or benzylic nature.

It is also possible to express the limitation on water-miscible polar organic solvent by indicating that the molar ratio of the amount of a possible miscible polar solvent, expressed in moles, to the sum, expressed in equivalents, of the cocations of the sulfide and of the possible base is advantageously at most equal to 1, preferably at most equal to 1.5, more preferably at most equal to 1/10.

Mention may be made, among the advantageous compounds to be synthesized, of the hydrofluoromethylene radical compounds of formulae I and IV' formula I formula IV'

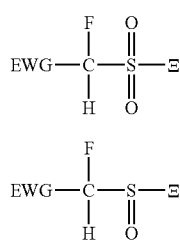

In this formula EWG is an electron-withdrawing group chosen from fluorine and those for which the σ$_p$ (Hammett constant) value is at least equal to 0.2, advantageously to 0.4, and Ξ represents either a halogen, advantageously chosen from chlorine and bromine, or an oxygen, itself carrying either a hydrogen or a negative charge.

The reaction of the stage can be written as follows

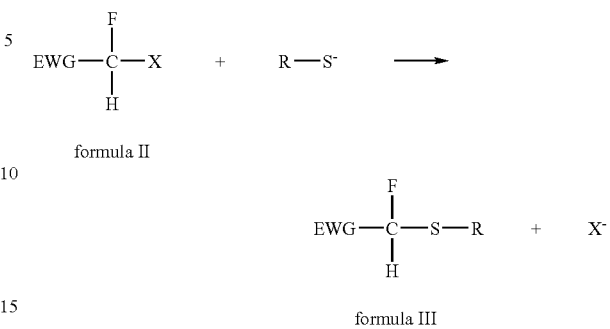

formula II formula III

In the above formulae, R represents an alkyl, that is to say an alcohol from which the OH functional group has been removed.

The halogenation reaction, which constitutes a preferred embodiment of stage b), can be symbolized by one or more of the reactions below:

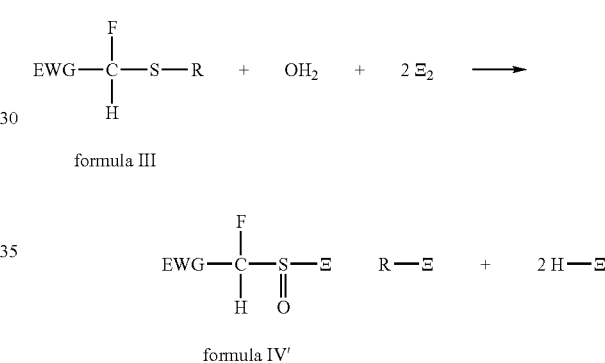

formula III formula IV' formula IV'

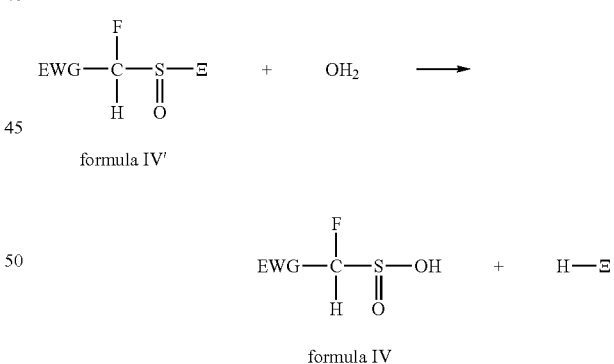

formula IV

In this reaction, it is found that the halogen, symbolized here by Ξ₂, oxidizes the sulfur, releases the alkyl radical in the form of an alkyl halide, R-Ξ and releases three acids H-Ξ. This reaction results in a sulfinic derivative. This sulfinic derivative appeared in this equation in sulfinic acid itself. On the other hand, it is possible to recover the intermediate derivative of IV', which may constitute a reactant of value, and, on the other hand, the reaction is not halted at this stage, unless the amount of halogen is limited, as the sulfinic acid is oxidized to sulfonic derivatives; this derivative can be either a sulfonyl halide, according to the following reaction:

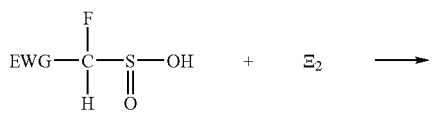

formula V

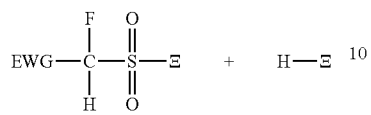

whereas, depending on the operating conditions, the reaction can result in the sulfonic acid or its salts, according to the reaction below:

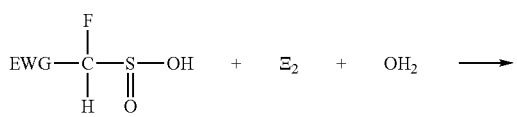

formula V

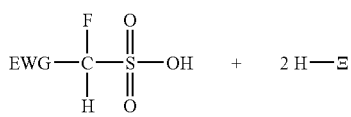

According to the present invention it could be shown that the operating conditions can be chosen in order to optimize the reaction either towards a sulfonyl halide or towards the sulfonic acid or its salts.

Thus, when it is desired to obtain an acid halide, it is desirable for stage b) to be carried out in the presence of a dissociated salt dissolved in aqueous phase, advantageously in an amount sufficient to reach and/or exceed a concentration of 1 N, preferably 2 N (as anion); the anion is advantageously a halide, preferably the halide corresponding to the acid halide desired. This is particularly true when the acid halide desired is the acid chloride and the sulfonyl chloride. When use is made of a halide from an atomic row higher than that of the halogen used, of course, the sulfonyl halide formed is that corresponding to the halide from the highest row in the medium.

Another characteristic which promotes the formation of the acid halide is the maintenance at a pH lying within a range from 4 to 9, advantageously from 5 to 8. As these two operating conditions are not in conflict, it is possible to combine them and thus to obtain a good result by using a saline solution at a pH ranging from 4 to 9.

It is preferable for the saline solution specified above to be a solution of an alkali metal halide (bromide and preferably chloride but not iodide) at a concentration of halide of at least 1 N, preferably of at least 2 N.

If it is desired to favor the formation of sulfonic acid, it is preferable then to be positioned at acid pH values, that is to say pH values at most equal to 2, preferably at most equal to 1, preferably in the vicinity of 0, and to avoid carrying out the chlorination or hydrolysis in a saline medium. It is thus advisable to avoid a salt content in the medium of greater than 1 N. It is also desirable, in order to lower the salt content, to separate the aqueous phase from the sulfide phase which is generally formed during stage a). When this sulfide phase has not been formed, it is then desirable to carry out a liquid/liquid or liquid/solid extraction in order to recover the sulfide, to drive off the solvent and subsequently to treat the sulfide phase in an aqueous phase, so as to bring about cleavage between the sulfur atom and the carbon atom of the alkyl bonded to the sulfur.

One of the advantages of the present invention is to be able to carry out the synthesis of a halide (bromide and advantageously chloride) in a single stage without changing the medium by carrying out the reaction in a concentrated aqueous medium in stage a) and by again using the aqueous medium, after optionally removing the miscible or immiscible solvents, and cleaving with formation of a sulfinyl or sulfonyl group, as described in stage b).

The reaction temperature is advantageously between 50° C. and 110° C., preferably between 60° C. and 90° C.

The pressure is relatively high due to the fact that the compounds exhibiting a carbon of $sp^3$ hybridization carrying a hydrogen, a fluorine and a heavy halogen are often volatile, as is the case when EWG is fluorine, and that the said compound and the compound used as coolant under the name of R-22 (that is to say, chlorodifluoromethane) are very volatile, which results in a high pressure in order to maintain the minimum of these compounds in a liquid phase and in particular an aqueous phase.

According to an advantageous form of the invention, the electron-withdrawing group, such as that which is represented by EWG in the preceding equations, is a highly fluorinated group; advantageously, the total carbon number of EWG (electron-withdrawing group), more specifically Rf, is between 1 and 15, preferably between 1 and 10.

Thus, the electron-withdrawing group is advantageously chosen from fluorine and the Rf groups; the term "Rf" is understood to mean a radical of formula:

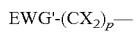

where the X groups, which are alike or different, represent a chlorine, a fluorine or a radical of formula $C_nF_{2n+1}$, with n being an integer at most equal to 5, preferably to 2, with the condition that at least one of the X groups is fluorine, fluorine advantageously carried by the carbon connected to the sulfur;

where p represents an integer at most equal to 2;

where EWG' represents an electron-withdrawing group (that is to say, $\sigma_p$ greater than zero, advantageously than 0.1, preferably than 0.2), the possible functional groups of which are inert under the conditions of the reaction, advantageously fluorine or a perfluorinated residue of formula $C_nF_{2n+1}$ with n being an integer at most equal to 8, advantageously to 5.

As has already been mentioned, one of the preferred uses of the invention is that which corresponds to the case where the electron-withdrawing group is fluorine, which implies that the compound is R-22, that is to say chlorodifluoromethane.

In the first stage, stage a), it is desirable for there to be a minimum amount of water and this minimum may be defined as follows. The ratio of the water, expressed in moles, to the cation present, more precisely the sum of the cations present, expressed in equivalents, is at least equal to 4, advantageously to 6, preferably to 8, in order to prevent the medium from being excessively polar and disturbing the solubility of the substrate comprising a carbon of $sp^3$ hybridization carrying a hydrogen, a fluorine and a heavy halogen.

Advantageously, the cation or cations present in aqueous phase are monovalent cations. It is preferable for these cations to be chosen from quaternary phosphoniums, quaternary ammoniums and alkali metal cations and advantageously the latter and, more preferably among the latter, the cations corresponding to sodium and corresponding to potassium.

In order to obtain satisfactory kinetics, it is preferable for the temperature to be at least equal to 80° C. in stage a).

During the reaction, the halide formed R-Ξ is recovered and then subjected to an alkali metal sulfide in order to reform the starting material, namely the mixed sulfide of alkyl and of cation.

starting substrate under consideration and CY is the conversion yield, that is to say the amount of desired product obtained divided by the amount of substrate under consideration which has disappeared.

The various tests carried out are summarized in the following table:

| Benzyl mercaptan | Sodium hydroxide mol.eq. | Solvent | PTC 5 mol % | Conc. benzyl mercaptan, % w/w | R-22 mol.eq. | Temp. (° C.) | DC (%) BT | RY (%) BDFS | CY (%) BDFS |
|---|---|---|---|---|---|---|---|---|---|
| 100 mmol | 2.5 ground | TCB (1,2,4-trichlorobenzene) | TDA-1 | 11 | 2 | 90 | 100 | 82 | 82 |
| " | 2.5 ground | " | " | 26 | 2 | 85 | 99.6 | 70 | 70 |
| " | 2.5 30% sol. | " | " | 26 | 2 | 85 | 77 | 71 | 93 |
| " | 1.1 30% sol. | " | " | 26 | 2 | 85 | 74 | 66 | 89 |
| " | 1.1 30% sol. | " | " | 26 | 2 | 50 | 52 | 48 | 92 |
| " | 1.1 30% sol. | " | No PTC | 26 | 2 | 90 | 67 | 59 | 87 |
| " | 1.1 30% sol. | $H_2O$ | No PTC | 33 | 3-4 | 95 | 80.7 | 74.3 | 92 |
| " | 1.1 30% sol. | $H_2O$ | TDA-1 | 33 | 4 | 95 | 80.7 | 74.6 | 92 |
| " | 1.1 KOH 50% | $H_2O$ | No PTC | 50 | 3 | 95 | 83 | 75 | 90 |
| " | 2 NaOH 30% sol. | $H_2O$ | " | 31 | 3 | 95 | 82 | 75 | 92 |
| 1.5 mol | 1.1 NaOH 30% | $H_2O$ | " | 33.4 | 1 P = 8.5 bar | 95 | 79 | 75.3 | 95 |

In the table, BT means benzylthiol, that is to say benzyl mercaptan.
BDFS means benzyl difluoromethyl sulfide.

The following nonlimiting examples illustrate the invention.

EXAMPLE 1

Synthesis of Benzyl Difluoromethyl Sulfide

One equivalent of 40% by weight of sodium hydroxide in water was mixed with one equivalent of benzyl mercaptan with R-22 (1.1 molar equivalents) at 60° C. for 1 h. The tests are carried out in a 500 ml Hastelloy reactor at an autogenous pressure at 60° C. The pressure is 3.5 bar. A chemical yield of 75%, by quantitative determination by $^{19}F$ NMR, is obtained over two tests carried out under the same conditions.

EXAMPLE 2

Variation in the Various Parameters of the Synthesis of Benzyl Difluoromethyl Sulfide from Benzyl Mercaptan The procedure described above was repeated, with the duration being modified and with a large excess of R-22 (chlorodifluoromethane) being introduced gradually. The reaction was carried out at atmospheric pressure over a period of 4 h.

The details of the operating conditions are shown in the table below, along with the various yields. It should be remembered that DC means degree of conversion. This is the ratio of the amount of substrate under consideration which has disappeared during the reaction to the starting amount. In this instance, the yield is calculated with respect to the benzyl mercaptan initially charged. The RY is the reaction yield, that is to say the amount of desired product with respect to the

EXAMPLE 3

Comparative Example

Role of the Water

The conditions of test 2k were repeated, the amount of water being significantly increased so that there are 5 mol of benzyl mercaptan per kg of water present in the phase. The result obtained shows a dramatic decline in the yield, namely yields of the order of 15%.

EXAMPLE 4

Chlorination Test 75 g of water are charged in a reactor and then 26.1 g of difluoromethylthiobenzyl are added.

The reaction medium is two-phase and colorless. The mixture is cooled to 10° C. and chlorine (32 g) is slowly introduced into the material.

In order to maintain the temperature at 10° C. despite the very high exothermicity, the jacket set temperature is regulated at −5° C.

The introduction of chlorine is halted when the exothermicity ceases and when the reaction medium begins to turn yellow.

The chlorine is introduced over 3 hours (31.6 exactly).

At the end of the 3 hours, the reaction medium is allowed to return to ambient temperature, flushing is carried out with nitrogen and stirring is halted. The two phases readily separate on settling. The aqueous phase is clear and colorless. The organic phase is clear and yellow.

The organic phase is dried over MgSO₄ and filtered through a sintered glass funnel.

37.6 g of liquid phase are recovered, the analysis of which by gas chromatography indicates a chemical yield of difluoromethanesulfonyl chloride of 82%.

After distillation, 14.3 g of difluoromethanesulfonyl chloride with a purity of greater than 99% are obtained (boiling point: 66° C. under 300 mbar).

What is claimed is:

1. A process for the synthesis of compounds having a hydrofluoromethylenesulfonyl radical from an alkyl thiolate, the process comprising the steps of:
   a) reacting (1) an alkyl thiolate and an associated cation with (2) a compound exhibiting a carbon of sp³ hybridization carrying a hydrogen, a fluorine, a heavy halogen selected from the group consisting of chlorine, bromine and iodine, and an electron-withdrawing group which is fluorine or a group having a Hammett constant ($\sigma_p$) value of at least equal to 0.2, in a solvent; and
   b) oxidizing the compound formed in step a) in the presence of an aqueous phase;
   said solvent of step a) being a water-immiscible solvent, an aqueous phase or a two-phase combination of a water-immiscible solvent and of an aqueous phase, said aqueous phase comprising at most ⅓ by weight of water-miscible nonaqueous solvent; with a ratio of the amount, in equivalents, of the alkyl sulfide to the amount, in moles, of water being at most equal to 50.

2. The process as claimed in claim 1, wherein the solvent of step a) further comprises a strong base with a pKa of the associated acid at least equal to 10, in an amount, expressed in equivalents, of at least equal to 5% of the amount of said thiolate.

3. The process as claimed in claim 2, wherein said amount of strong base is at most equal to the amount of said thiolate.

4. The process as claimed in claim 2, wherein, in step a), the solvent further contains a polar solvent with a molar ratio of the amount of said polar solvent, expressed in moles, to the sum, expressed in equivalents, of the co-cations of the sulfide and of the base is at most equal to 1.

5. The process as claimed in claim 1, wherein the electron-withdrawing group is fluorine or a (Rf) groups of formula:

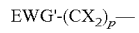

Wherein:
   the X groups, which are identical or different, represent a chlorine, a fluorine or a radical of formula $C_nF_{2n+1}$, with n being an integer at most equal to 5, with the proviso that at least one of the X groups is fluorine;
   p represents an integer at most equal to 2; and
   EWG' represents an electron-withdrawing group.

6. The process as claimed in claim 5, wherein the total number of carbon atoms in the group Rf is between 1 and 15.

7. The process as claimed in claim 1, wherein the electron-withdrawing group is fluorine.

8. The process as claimed in claim 1, wherein the ratio of the water, expressed in moles, to the cation, expressed in equivalents, is at least equal to 4.

9. The process as claimed in claim 1, wherein said cation is monovalent.

10. The process as claimed in claim 9, wherein said cation is phosphonium, a quaternary ammoniums or an alkali metal.

11. The process as claimed in claim 1, wherein stage b) is carried out either in the presence of a dissociated salt dissolved in the reaction mixture or by maintaining a pH within the range from 4 to 9, in order to obtain an acid halide.

12. The process as claimed in claim 1, wherein the process is carried out at a temperature at least equal to 80° C.

* * * * *